(12) United States Patent
Guo et al.

(10) Patent No.: US 7,595,196 B2
(45) Date of Patent: Sep. 29, 2009

(54) LATERAL FLOW ASSAY DEVICES WITH INHIBITING BACKFLOW OF THE SAMPLE AND METHODS OF USE

(75) Inventors: Huiyan Guo, San Diego, CA (US); Simin Zhu, San Diego, CA (US); Welson Wu, Hangzhou (CN); Soar Gao, Hangzhou (CN); Dale Dai, Hangzhou (CN)

(73) Assignee: Oakville Hong Kong Company Limited, Central (HK)

( * ) Notice: Subject to any disclaimer, the term of this patent is extended or adjusted under 35 U.S.C. 154(b) by 765 days.

(21) Appl. No.: 10/948,093

(22) Filed: Sep. 23, 2004

(65) Prior Publication Data

US 2005/0079629 A1    Apr. 14, 2005

Related U.S. Application Data

(60) Provisional application No. 60/505,708, filed on Sep. 23, 2003, provisional application No. 60/508,608, filed on Oct. 3, 2003.

(51) Int. Cl.
*G01N 31/16* (2006.01)
*G01N 31/22* (2006.01)

(52) U.S. Cl. .......... 436/163; 436/174; 422/56; 422/57; 422/58; 422/61; 422/68.1

(58) Field of Classification Search .......... None
See application file for complete search history.

(56) References Cited

U.S. PATENT DOCUMENTS

| | | |
|---|---|---|
| 3,718,543 A | 2/1973 | Lagomarsino |
| 3,785,929 A | 1/1974 | Kronish |
| 3,811,840 A | 5/1974 | Bauer |
| 4,063,894 A | 12/1977 | Ogawa |
| 4,160,008 A * | 7/1979 | Fenocketti et al. ............ 422/56 |
| 4,275,149 A | 6/1981 | Litman et al. |
| 4,299,916 A | 11/1981 | Litman et al. |
| 4,631,255 A | 12/1986 | Takino |

(Continued)

FOREIGN PATENT DOCUMENTS

EP    0 462 376    4/1991

(Continued)

OTHER PUBLICATIONS

"Drugs of abuse testing division http://www.onsite-dat.com/flash/train_adulta.htm DWWW-Feb. 8, 2001" ADULTACHECK, 2000, pp. 1-3 XP002159963.

*Primary Examiner*—Yelena G Gakh
(74) *Attorney, Agent, or Firm*—Fred C. Hernandez; Mintz, Levin, Cohn, Ferris, Glovsky and Popeo P.C.

(57) ABSTRACT

The present invention is directed novel lateral flow devices for analyzing liquid samples. The devices contain chemical test strips and are useful for testing liquids for physical properties, such as pH, specific gravity, contamination or adulteration, the presence of proteins or blood, and the like. The test strips contain a bibulous material, a filter element, a reagent pad, and in some embodiments also contain a hydrophobic member and a cover. Any fluid can be tested, for example, urine or other body fluids, environmental samples, biological samples, clinical samples, or food and beverage samples.

17 Claims, 2 Drawing Sheets

U.S. PATENT DOCUMENTS

| | | |
|---|---|---|
| 4,744,952 A | 5/1988 | Ogita |
| 4,795,611 A | 1/1989 | van der Smissen |
| 4,960,710 A | 10/1990 | Lau |
| 5,096,833 A | 3/1992 | Lau |
| 5,403,551 A | 4/1995 | Galloway |
| 5,415,994 A * | 5/1995 | Imrich et al. .................. 435/5 |
| 5,418,143 A * | 5/1995 | Zweig .......................... 435/13 |
| 5,491,094 A | 2/1996 | Ramana |
| 5,811,254 A | 9/1998 | Wu |
| 6,087,089 A | 7/2000 | Wu |
| 6,379,620 B1 | 4/2002 | Tydings |
| 6,503,726 B2 | 1/2003 | Anne |
| 6,514,769 B2 | 2/2003 | Lee |
| 6,537,823 B1 | 3/2003 | Smith |
| 6,548,019 B1 | 4/2003 | Lee |
| 6,566,051 B1 | 5/2003 | Owens |
| 6,673,632 B1 | 1/2004 | Ohshiro |
| 6,818,452 B2 | 11/2004 | Wong |
| 2002/0001854 A1 | 1/2002 | Lee |
| 2002/0086435 A1 | 7/2002 | Fernandez Decastro |
| 2002/0098512 A1 | 7/2002 | Goodell et al. |
| 2002/0155028 A1 | 10/2002 | Wong |
| 2003/0007892 A1 | 1/2003 | Smith |
| 2003/0013206 A1 | 1/2003 | Takahasi et al. |
| 2003/0027350 A1 | 2/2003 | Smith |
| 2003/0032196 A1 | 2/2003 | Zhou |
| 2003/0045003 A1 | 3/2003 | Smith |
| 2003/0186451 A1 | 10/2003 | Smith |
| 2004/0018636 A1 | 1/2004 | Zhou |

FOREIGN PATENT DOCUMENTS

| | | |
|---|---|---|
| WO | WO 00/42430 | 7/2000 |
| WO | 00/62060 | 10/2000 |
| WO | WO 01/75444 | 10/2001 |
| WO | WO 01/83930 | 11/2001 |
| WO | WO 02/08729 | 1/2002 |
| WO | 2005/031351 | 4/2005 |

* cited by examiner

LATERAL FLOW ASSAY DEVICES WITH INHIBITING BACKFLOW OF THE SAMPLE AND METHODS OF USE

This application claims priority to U.S. provisional patent application Ser. No. 60/505,708, filed Sep. 23, 2003, and to U.S. provisional patent application Ser. No. 60/508,608, filed Oct. 3, 2003.

FIELD OF THE INVENTION

The present invention is directed to the analysis of fluids for the presence of analytes or adulterants, and other physical properties.

BACKGROUND OF THE INVENTION

The following Background of the Invention is intended to aid the reader in understanding the invention and is not admitted to be prior art.

Fluids are routinely tested for contents and physical characteristics, which indicate the status of the source of the fluid. For example, biological fluids are tested for indicators of health status and contaminants, such as oxidants, pH, specific gravity, creatinine, bilirubin, glucose and the like. Food and beverages are tested for pH, specific gravity and evidence of contamination by bacteria or toxic substances. Soil and water samples are also tested for pH, specific gravity and contaminants such as bacteria, lead or mercury.

In general, these rapid chemical tests have been conducted using non-wicking dip-and-read test strips that have a series of chemical test pads. The pads change color due to a chemical reaction with the sample or a sample component. In general, the operator dips the strip into a liquid and then observes the test pads for color changes. The color of a test pad is compared to a results card, to determine the result of the test.

The dip-and-read test strips have many drawbacks. In particular, they are not amenable to incorporation into today's new rapid immunoassay test devices. However, it is still necessary to perform these chemical tests. These new rapid immunoassay test devices are designed to limit contact between the sample and the operator. But, to perform the dip-and-read chemical tests the operator must open the device and expose themselves to contamination with the sample and the sample to contamination by the operator or by other reagents on the test strip.

There is therefore a need for better methods and apparatuses for performing adulteration testing of samples.

SUMMARY OF THE INVENTION

The present invention is directed to devices and methods for the rapid chemical analysis of liquid samples. In one embodiment the invention provides lateral flow test strips that test for physical properties of the sample. The devices and methods of the invention are applicable in a wide variety of formats where it is desirable to detect the presence of contamination or adulteration in a liquid or liquefied sample. For example, the devices can detect the pH, the specific gravity, and the presence of adulterants that are sometimes added to a collected sample of urine by a patient wishing to disguise the use of illegal drugs. In other examples the devices and methods can be used to detect the presence of contaminating bacteria in food samples, or the presence of lead or other undesirable substances or analytes in food or beverages.

In a first aspect the present invention provides devices for analyzing a liquid sample. The devices contain a test strip that has a bibulous material for transporting liquid sample through the test strip; a filter member in liquid communication with the bibulous material, and a reagent pad in liquid communication with the filter member. The test strip contains reagents for detecting a property of the liquid sample. The reagent pad contains reagents for producing a detectable signal related to a property of the sample. In one embodiment the device also contains a cover. The filter member is made of a material that inhibits backflow of fluid from the reagent pad to the bibulous material. By "inhibits backflow" is meant that any quantity of fluid that flows from the reagent pad to the bibulous material is not of a quantity that will change the result of the assay or transport reagents onto the bibulous material or into an neighboring reagent pad in an amount that is detectable in the assay or obscures the result of the assay. In some embodiments of the invention, the device also contains a support positioned under the bibulous material. The liquid sample is transported through the test strip by capillary action. "Capillary action" refers to the well-known physical effect caused by the interactions of a liquid with the walls or interior of a material where, which results in a movement of the liquid through the material.

In one embodiment the test strips also contain a hydrophobic member positioned between a portion of the filter member and the bibulous material. The hydrophobic member is positioned to inhibit backflow of sample from the reagent pad into the bibulous material. In various embodiments the cover of the test strip can be an adhesive tape or glue, a mesh, and can be painted, printed or sprayed onto the test strip. The cover can also laminate the test strip and thereby hold the parts of the test strip together, such as the reagent pad, filter member, and bibulous material. In one embodiment the reagent pad is visible to the operator through the cover. By a "bibulous material" is meant a material that readily absorbs or imbibes fluids and in which capillary action serves to transport the fluid to other portions of the material. A "filter member" promotes even distribution of liquid sample as sample flows to the reagent pad. This in turn promotes an even development of detectable signal in the reagent pad. The filter member also inhibits backflow of sample from the reagent pad to the bibulous material, and therefore also inhibits movement of reagent chemicals from one reagent pad to another. By a "hydrophobic member" is meant a member that does not allow the passage of a quantity of fluid that would alter the result of the assay. The hydrophobic member will usually be a hydrophobic barrier to fluid movement.

In various embodiments the sample being tested can be a biological fluid such as urine, or an environmental sample, or a food or beverage sample, depending on the property of the sample being tested or analyzed. In various embodiments the sample can be a bodily fluid, derived from a tissue or derived from a bodily fluid, blood, serum, plasma, saliva, oral fluid, sweat, urine, feces, spinal fluid, vaginal swabs, mucus, tissue, milk, wine, food, water and soil. The sample can also be a liquid derived from a solid. By "derived from a solid" is meant that the sample is transformed into a liquified form from a solid form. A wide variety of liquid samples can be tested with the device of the present invention. The samples may already be liquids or they may be derived from solids or semisolids by mixing or solubilization with a liquid.

In other embodiments analysis of the sample can involve the determination of a property of the sample. The "property of the sample" can be any property of the sample, for example, the determination of the presence of an analyte or the determination of a physical property of the sample. In various embodiments the analyte can be an oxidizing agent, a reducing agent, a nitrate, a nitrite, glutaraldehyde, pyridinium chlorochromate, heavy metals, toxic metals, toxic chemicals, blood, a blood component, a blood product, glucose, ketones, peroxide, protein, creatinine, urobilinogen, bilirubin, bacteria, bacterial components and bacterial products. In other embodiments the physical property is the pH or specific gravity of the sample, or the presence of protein, bacteria, or blood cells.

In another aspect the present invention provides methods of analyzing liquid samples. The methods involve exposing a first end of the device described herein to a liquid sample; allowing sufficient time for the reagent pad to react with the sample and provide a detectable signal, and comparing the signal to a standard. In some embodiments the detectable signal can be a change in the color of the reagent pad. The "standard" can be any convenient and objective measure of the result of the assay. For example, the standard can be a standard comparison chart or card that is provided on or with the device or is otherwise available, and the comparison of the signal to the standard can involve comparing the color of the reagent pad after the assay to colors on a standard chart or card. By matching the color of the reagent pad to the chart or card, a value or result of the assay is obtained. But the detectable signal can be any objective indicia of the result of the assay (e.g., fluorescence, enzymatic based detection, spectrophotometric detection, etc.). The standard can be based on any of these or other detection methods. The methods can also involve allowing sufficient incubation time for sample to flow along the absorbent strip and into the test pad and for reagents in the test pad to react with the sample, and, at the end of the incubation, comparing the color of the test pad to a chart or card that relates a test pad color with an assay result.

In another aspect the present invention provides kits for analyzing a liquid sample. The kits include a device of the present invention in a package with instructions for use. In different embodiments the kit can also include an assay result comparison chart or other standard. The kit can be packaged in any convenient format, for example, in a box or in a plastic wrapping, or in a foil pouch, which can be vacuum-sealed.

The present invention includes a variety of other useful aspects, which are detailed herein. These aspects of the invention can be achieved by using the articles of manufacture and compositions of matter described herein. To gain a full appreciation of the scope of the present invention, it will be further recognized that various aspects of the present invention can be combined to make desirable embodiments of the invention. In addition, a variety of other aspects and embodiments of the present invention are described herein.

The summary of the invention described above is not limiting and other features and advantages of the invention will be apparent from the following detailed description, as well as from the claims.

DETAILED DESCRIPTION

Lateral Flow Chemical Test Strips

In the following detailed description, reference is made to the accompanying drawings that form a part hereof, and in which is shown by way of illustration specific embodiments in which the invention may be practiced. It is understood that other embodiments may be utilized and structural changes may be made without departing from the scope of the present invention.

Figure 1:
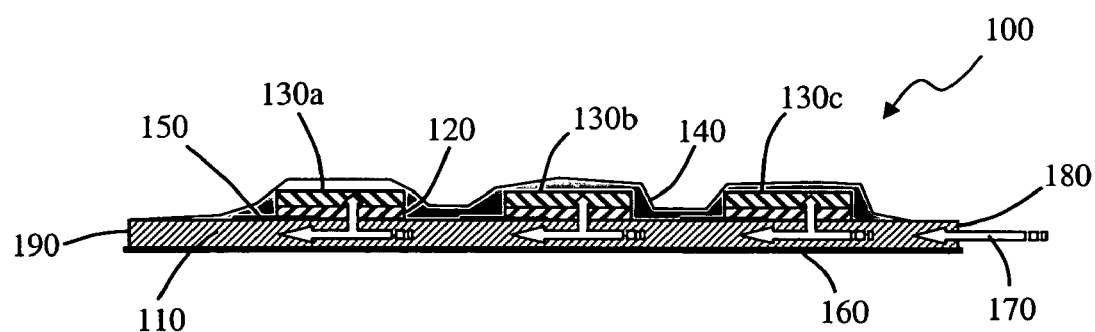
FIG. 1 provides a cross-section of the present invention. Bold arrows 170 illustrate sample flow.
Figure 2:
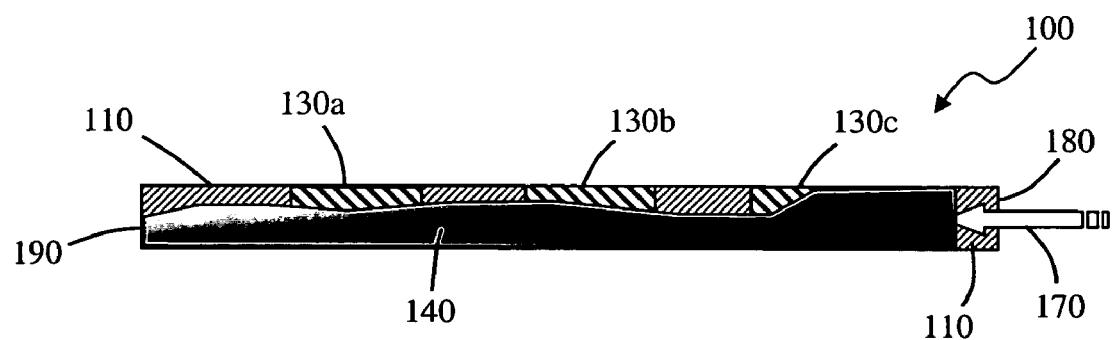
FIG. 2 provides a top view with a cutaway portion of a device of the present invention.

FIG. 1 shows one embodiment of the present invention, a lateral flow test strip 100 of the present invention. The test strip comprises a bibulous material 110, a filter member 120, a reagent pad 130 and a cover 140. The bibulous material 110 can be made of any material that supports capillary flow, such as but not limited to polyamide fiber, polyester, filter paper, nitrocellulose, hydrophilic meshes, glass meshes treated to become hydrophilic, and the like. The bibulous material 100 is a wicking material that can freely wick liquid sample (shown as large arrows, 170) from one end of the strip to the other end within a period of time necessary to conduct a valid assay. This will usually be a matter of a few minutes.

Many different bibulous materials will find use in the present invention. Any material that has a liquid wicking quality and efficiently transports liquid can be used as the bibulous material. In one embodiment the bibulous material is a polyamide fiber. Membrane thicknesses of between 0.6 and 1.0 mm are useful. The bibulous material is absorptive in its nature, and in this embodiment a polyamide fiber material of 60 mm×10 mm will absorb 0.6 gm of fluid, +/−0.15 gm. Such polyamide fibers are available as wicking material from Filtrona Fibertec™ (Colonial Heights, Va.). Of course other bibulous materials also find use in the invention. For example, surface active media that are often used as filtering materials and utilize either amine or carboxyl groups on the surface of the fiber as substrates for a wide variety of linking agents can also be used. This material also functions well in the present invention as bibulous material when supplied as a sheet or strip, and is available from Filtrona Fibertec™ (Colonial Heights, Va.). Other embodiments include, but are not limited to, the use of cotton fiber. Polyester is another material that is useful as a bibulous material and is advantageously treated according to methods known in the art with detergents, proteins, and buffers.

The bibulous materials used in the invention have a contact point 180 for the liquid sample, which is the point where the test strip is introduced into or exposed to the sample and the point where a liquid sample enters the bibulous material. In one embodiment the test strips of the invention have a single contact point 180, i.e., sample is introduced into the bibulous material at one point on the bibulous material. In another embodiment of the test strips each of the filter members and hydrophobic members (when present) in the test strip contact the same strip of bibulous material. In some embodiments the test strips of the invention comprise a single strip of bibulous material that is contacted at various points along the strip of bibulous material with filter members and reagent pads that test for different properties of the liquid sample. The test strips of the present invention can also be constructed so that they comprise a single piece of bibulous material, 2 or more filter members and reagent pads (and optionally hydrophobic members) that may be spaced sequentially along the bibulous material, and a single cover. Of course multiple test strips can be included in any particular device depending on the nature of the assays being performed. The bibulous material is normally in the shape of a rectangle or strip, but can also be provided in any other shape that does not distort the results of the assay. In one embodiment the test strips of the invention contain at least 2 reagent pads that test for different properties of the sample. In other embodiments the test strips contain at least 3, at least 4, at least 5, at least 6, or at least 7 reagent pads. In some embodiments the test strips will have a generally rectangular shape, and the filter members and reagent pads are spaced generally equidistant from each other along the bibulous or absorbent material.

The bibulous materials used in the invention have a contact point 180 for the liquid sample, which is the point where the test strip is introduced into or exposed to the sample and the point where a liquid sample enters the bibulous material. In one embodiment the test strips of the invention have a single contact point 180, i.e., sample is introduced into the bibulous material at one point on the bibulous material. In another embodiment of the test strips each of the filter members and hydrophobic members (when present) in the test strip contact the same strip of bibulous material. In some embodiments the test strips of the invention comprise a single strip of bibulous material that is contacted at various points along the strip of bibulous material with filter members and reagent pads that test for different properties of the liquid sample. The test strips of the present invention can also be constructed so that they comprise a single piece of bibulous material, two or more filter members and reagent pads (and optionally hydrophobic members) that may be spaced sequentially along the bibulous material, and a single cover. Of course multiple test strips can be included in any particular device depending on the nature of the assays being performed. The bibulous material is normally in the shape of a rectangle or strip, but can also be provided in any other shape that does not distort the results of the assay. In one embodiment the test strips of the invention contain at least two reagent pads that test for different properties of the sample. In other embodiments the test strips contain at least three, at least four, at least five, at least six, or at least seven reagent pads. In some embodiments the test strips will have a generally rectangular shape, and the filter members and reagent pads are spaced generally equidistant from each other along the bibulous or absorbent material.

Reagent pad 130(*a-c*) contains the reagents necessary to assay for and provide a detectable signal that correlates with a property of the sample. In those embodiments where the reagent pad is a chemical test pad, those chemical test pads available in the art are useful in the present invention. These may include pads of the "dip-and-read" test strip format and typically include a pad imbued with chemical indicators that produce a detectable signal in response to a property of the sample being assayed that has come into contact with the test pad. Some currently available test pads are summarized in the table below.

| Physical Property/Test For | Test Name | Possible Indicator Of . . . |
|---|---|---|
| pH | pH | Sample contamination or adulteration, disease states |
| Specific Gravity | Specific Gravity | Sample dilution, disease states |
| Bleach, peroxide, etc | Oxidant | Sample adulteration |
| Creatinine | Creatinine | Sample dilution, disease states |
| Nitrite and Nitrate | Nitrite/Nitrate | Sample adulteration, disease states |
| Glutaraldehyde | Glutaraldehyde | Sample adulteration |
| Protein (specific or nonspecific) | Protein | Disease states |
| Blood, Leukocytes | Blood/Leukocytes | Disease states |
| Sugar | Sugar | Disease states/Diabetes |
| Heavy metals, Toxins, etc. | Heavy metals, Toxins, etc. | Sample or environmental contamination, poisoning |
| Ascorbic Acid | Vitamin C | Inhibitor of other tests (i.e. protein, blood, sugar, etc.); there may be too much in the diet |

-continued

| Physical Property/Test For | Test Name | Possible Indicator Of . . . |
|---|---|---|
| *E. coli* 0157: H7, *S. aureus*, *Salmonella*, *C. perfringens*, *Campylobacter*, *L. monocytogenes*, *V. parahaemolyticus*, *B. cereus* | Bacterial Contamination | Contaminated food or drink |
| Tumor markers | Tumor markers | Disease states |

Depending upon the intended use of the test strip of the invention, several different reagent pads may be placed on a single strip, and many different formats and embodiments are applicable to the present invention. For example, when the invention is used to test for drugs of abuse or their metabolites in urine, one would want to determine if the donor had adulterated the urine sample prior to providing it in an effort to mask the use of drugs of abuse. In this circumstance, a test strip can be equipped with pH, specific gravity, oxidants and nitrite indicators. Testing for these properties will reveal whether such adulteration has occurred because the great majority of known and popular adulterants will provide a suspicious result on one or more of these reagent pads, which can then be investigated further. The reagent pad can be made of 3MM filter paper, but other types of filter paper and other materials can also be used.

In other embodiments, an obstetrician might utilize a urinalysis test strip including assays for pH, specific gravity, protein, sugar, and/or other specific metabolic markers in each expectant mother's urine in order to screen for metabolic or other gestational problems. In other medical contexts one might employ a test strip with reagent pads for pH, specific gravity, protein, and blood to aid in determining if the patient has a bladder infection. In another circumstance, health inspectors might use test strips to test beef samples for contamination with *E. coli*0157:H7 or *Salmonella*. With reference to the present disclosure the person of ordinary skill will realize many additional contexts and combinations of reagent pads that will provide important information in these many contexts, which are also within the scope of the present invention.

Cover 140 provides protection to the test strip. In one embodiment cover 140 is adhesive and holds the components of the test strip together, for example, the bibulous material, filter element, hydrophobic member (when present), and reagent pad. Cover 140 may be made of any convenient material, as long as the reagent pads 130 are visible through the cover 140. In some embodiments, clear adhesive tape is used as the cover 140. In other embodiments, cover 140 is a clear mesh. In various embodiments the mesh can be made of nylon, polyester, fibrin, or other materials that are suitable for use as a cover. The cover 140 may be applied to the strip by any suitable manufacturing method, such as painting or spraying onto the strip. For example, a clear, water impermeable paint or ink can be painted onto the strips, to protect the strip and laminate the layers together.

Referring to FIG. 1, in additional embodiments a hydrophobic member 150 is positioned between absorbent member 110 and filter member 120. Hydrophobic member 150 may cover that portion of the diameter of the filter member necessary to inhibit backflow. For example, from about 25% to about 75% of the filter member 120 can be blocked by the hydrophobic member 150. In various other embodiments about 30% or about 40% or about 50% or about 60% of the filter member 120 is blocked by the hydrophobic member 150. Hydrophobic member 150 may be made of any suitable material that can inhibit or prevent the passage of liquid sample from the reagent pad 130 back to the bibulous material 110. In one embodiment the hydrophobic member is an adhesive barrier. AS-110 acrylic medical grade adhesive is a pressure-sensitive adhesive that is advantageously used, but other types of materials can also be used as the member. For example, the hydrophobic member can be made of water-insoluble adhesive, adhesive tape, any type of plastic, foil, glass, paint, or ink. In some embodiments, the hydrophobic member 150 is adhesive. By "about" is meant plus or minus 10%.

In other embodiments of the present invention, a support 160 is utilized to support and provide a backing for the test strip. Support 160 may be made of any convenient material, such as, for example, plastic, non-absorbent paper or cardboard, glass, metal or foil. The support can be positioned as a backing underneath the bibulous material.

When the first end 180 of test strip 100 is exposed to a liquid sample, the fluid wicks along the bibulous material 110 toward the second end 190 of test strip 100. When the sample reaches a filter member 120, a portion of the sample passes through the filter member 120 and then into the reagent pad 130. The remaining portion of the sample continues to wick toward the second end 190 of test strip 100. The filter member is made of a material (e.g., fiberglass) such that it inhibits the flow of fluid from the reagent pad back into the bibulous material. The hydrophobic member (when present) also serves to block fluid flow from the reagent pad into the bibulous material.

Without wanting to be bound by any particular theory, it is believed that a flow of fluid otherwise occurs in a "loop" direction, from the bibulous material through the filter member and into the reagent pad, and then back from the reagent pad through the filter element and finally into the bibulous material. The design of the present invention effectively blocks the flow of fluid back into the bibulous material. This results in a clearer assay result, and also results in the liquid sample being permitted to flow through the test strip for a longer period of time without obscuring the results of the assay. Because the liquid sample can remain in the bibulous material for a longer period of time, the test strip can incorporate a larger number of reagent pads than have been previously possible, and still produce clear and unambiguous assay results.

When the liquid sample passes into a reagent pad 130, reagents present within reagent pad 130 can react with analytes present the sample and produce a detectable signal, which provides the result of the assay. The reagents can also react with the liquid sample to determine a property of the sample (e.g., a physical property such as pH or specific gravity). By "reagents" is meant chemical substances that react in the presence of sample and produce a detectable signal and assay result. The detectable signal may be compared with a standard. In one embodiment, the detectable signal is a change in the color of the reagent pad, which can be compared with a standard chart or card illustrating colors that correlate with positive and/or negative results, or can also provide a quantitative value that correlates with an assay result. Using pH as an example, in one embodiment the reagent pad starts out beige and (for example) turns yellow after reacting with sample, this result indicates that the pH is low (acidic). If (for example) the pad turns blue after reacting with sample, this result indicates that the pH is high (basic). Middle pH values correlate with a color produced in the reagent pad that is in between yellow and blue, such as yellow green or greenish blue.

Types of Samples

Samples that can be tested with the device of the present invention include liquids of biological origin (e.g., body fluids and clinical samples). Liquid samples may be derived from solid or semi-solid samples, including feces, biological tissue, food samples. Such solid or semisolid samples can be converted into a liquid sample by any suitable method, for example by mixing, chopping, macerating, incubating, dissolving or enzymatically digesting solid samples in a suitable liquid (e.g., water, phosphate-buffered saline, or other buffers). "Biological samples" include samples derived from living animals, plants, and food, including for example urine, saliva, blood and blood components, cerebrospinal fluid, vaginal swabs, semen, feces, sweat, exudates, tissue, organs, tumors, tissue and organ culture, cell cultures and conditioned media therefrom, whether from humans or animals. Food samples include samples from processed food components or final products, meat, cheese, wine, milk and drinking water. Plant samples include those derived from any plant, plant tissue, plant cell cultures and conditioned media therefrom. "Environmental samples" are those derived from the environment (e.g., a water sample from a lake or other body of water, effluent samples, soil samples, ground water, ocean water, and runoff water. Sewage and related wastes can also be included as environmental samples.

The above listed samples are provided by way of example. With reference to the present disclosure the person of ordinary skill in the art will realize many other types of samples that can be analyzed in the context of the present invention.

Methods of Use

The present invention also provides methods of using a device of the invention. In one example, the first end 180 of a test strip 100 is exposed to a liquid or liquefied sample. The test strip is allowed to stay in contact with the sample for a brief period of time, such as from about 1 to about 10 minutes, or for that amount of time necessary for the liquid sample to be distributed to the reagent pads. The sample moves by capillarity from first end 180 to second end 190, and into the reagent pads 130 to react with the reagents on the pads. After reacting with the reagents in the reagent pads, the detectable signal of the reagent pads (e.g., a color change) is compared to a standard (e.g., a standard color chart). This can be done in any convenient manner, for example by visual inspection with the unaided eye, or using an electronic reader or scanner.

In another embodiment, the test strip 100 is incorporated into a test device, such as a lateral flow urinalysis cup. For example, test strip 100 may be incorporated into a drug of abuse test strip or a multi-drug panel or device, so that a technician can determine if the urine donor adulterated the sample in an effort to mask illegal drug use.

In another example, test strip 100 may be incorporated into a urine cup for use in a physician's office. In this situation, the technician would not have to directly handle the urine sample. Either the test would run when urine entered the cup (as in a "no-step" cup) or the technician could activate the test device portion of the cup (as in a "one-step" or "two-step" cup).

Kits

The present invention also provides test kits, including one or more test strips 100 of the invention. These test strips can be included in the kit with a standard chart, for example a color chart for interpreting the results of the assays where a color change is the basis for the assay result. The kit may also include instructions for use of the devices of the invention. Test strips 100 could be provided in a variety of formats, such as canisters of multiple test strips, as various types of urine cups or sample cups, as part of a saliva test device, or the like.

EXAMPLE 1

Construction of Test Strips

Test strips were constructed as sheets containing multiple test strips, which were later cut to produce individual test strips. A completed sheet was constructed by placing a 10.16 cm×27.94 cm pressure-sensitive adhesive backing card on a lab bench with the adhesive side up. The protective paper was peeled from the card, to expose the adhesive. A polyamide fibrous absorbent material of the same dimensions (Filtrona Fibertec™) was placed on top of the adhesive backing card. Three narrow strips of water-insoluble adhesive of dimensions about 0.2×27.9 cm (AS-110 acrylic medical grade adhesive) were laid down at regularly spaced intervals of 0.5 to 0.8 cm. Fiberglass strips of about 0.5 cm×27.9 cm were laid on top of the adhesive and the absorbent material, such that about 0.25 cm of the fiberglass overlapped the adhesive and 0.25 cm of the fiberglass was in direct contact with the absorbent material. Next, 0.5 cm×27.9 cm 3MM paper reagent pad strips were laid on top of the fiberglass strips. Each reagent pad strip covered the fiberglass strip below but not the absorbent (bibulous) material. Prior to application to the sheet, each reagent pad strip had been previously treated with reagents for detection of an analyte of interest and then dried. One reagent pad strip was prepared for the detection of creatinine, another for detection of nitrite, and the last for detection of glutaraldehyde. After application of the reagent strips, the sheet was covered with clear, pressure-sensitive adhesive film. The completed layered sheet was then cross-cut to produce individual test strips (about 0.5 cm wide), each individual strip having a creatinine pad, a nitrite pad and a glutaraldehyde pad.

EXAMPLE 2

Urine Testing for Adulteration 5 ml aliquot test solutions were prepared according to the following methods.

Creatinine Urine Analysis: Pooled urine having an initial creatinine concentration of 140 mg/dl was diluted with deionized water to give creatinine concentrations of 10 mg/dl, 20 mg/dl, 50 mg/dl and 100 mg/dl.

Nitrite Urine Analysis: Four 5 ml aliquots of nitrite-negative pooled urine were spiked with nitrite to give final concentrations of 0 mg/dl, 20 mg/dl, 50 mg/dl and 100 mg/dl.

Glutaraldehyde Urine Analysis: Glutaraldehyde-negative pooled urine aliquots were spiked with glutaraldehyde to give the following concentrations: 50 mg/dl, 100 mg/dl, 500 mg/dl and 2000 mg/dl glutaraldehyde.

Three test lots of strips were made, as described above in Example 1. Tests were conducted on three separate days, using 5 strips from each lot of strips with each concentration of adulterant. Thus, each concentration of adulterant (creatinine, nitrite or glutaraldehyde) was tested 45 separate times. Individual test strips were dipped into the sample for 1~2 seconds. The excess solution was absorbed by placing the strip on paper towels. Test results were read at 1-2 minutes and compared to a color chart. Test results were recorded.

The creatinine test pads changed from white to brown in the presence of creatinine. Each of the creatinine test pads analyzed gave the correct test result based on the known starting concentration. Creatinine samples containing 10 mg/dl and 20 mg/dl were clearly distinguishable based on unaided observation of the change in color of the reagent pads.

The nitrite test pads changed from white to pink in the presence of nitrite. Each of the nitrite test pads analyzed produced the correct test result based on the known sample concentrations. The nitrite test pads were clearly distinguishable between the 20 and 50 mg/dl levels based on an unaided observation of the color change of the reagent pad.

Glutaraldehyde and oxidants are not normal components of urine and their detection is an indication that the urine may have been adulterated. In the presence of glutaraldehyde, the glutaraldehyde test strips changed from intense rose to purple. All glutaraldehyde reagent pads tested gave the correct test result based on the known starting concentrations. The glutaraldehyde reagent pads were clearly distinguished between the 0 and 50 mg/dl levels based on unaided observation of the color change of the reagent pads.

EXAMPLE 3

Obstetrician's Office

This example illustrates the use of an embodiment of the invention for medical screening during pregnancy. In the medical office, a test strip is utilized that has reagent pads for the testing of sugar, protein, creatinine, blood, and pH. The test strip is dipped into a sample of urine from a pregnant patient. The urine wicks to the second end 190 of the test strip. The assay result is compared with a standard chart. If the assay indicates an abnormal result for any of the test included in the test strip, further testing and/or evaluation can be ordered.

EXAMPLE 4

Pre-Employment Drug Screening

This example illustrates the use of the invention in the context of pre-employment drug screening. A prospective employer acquires test strips of the invention containing tests for drugs of abuse. A "drug of abuse" is a drug that is taken for non-medicinal reasons (usually for mind-altering effects). The abuse of such drugs can lead to physical and mental damage and (with some substances) dependence and addiction. Examples of drugs of abuse include cocaine, amphetamines (e.g., black beauties, white bennies, dextroamphetamines (dexies, beans), methamphetamines (crank, meth, crystal, speed)), barbiturates, lysergic acid diethylamide (LSD), depressants, sedatives (e.g., selective serotonin reuptake inhibitors), phencyclidine (PCP), tetrahydrocannabinol (THC), and opiates (e.g., morphine, opium, codeine, and heroin). For this testing purpose it is also desirable to utilize test strips that incorporate assays for the adulteration of urine. For example, in some formats creatinine and protein assays may be included on the test strip to detect the dilution of a urine sample. B-vitamins may also be tested for, or any of glutaraldehyde, nitrites, chromate, vinegar, Visine™ (Pfizer, Inc., New York, N.Y.), sodium bicarbonate, Drano™ (S.C. Johnson, Racine, Wis.), soft drinks, oxidants such as bleach, hydrogen peroxide, pyridinium, chlorochromate, or other chemicals added to urine in attempts to adulterate. The invention can be utilized in an convenient format such as a urine cup format.

The prospective employee is sent to a testing facility for drug testing. When a urine cup format is utilized the patient introduces sample into the cup. A test strip of the invention is incorporated into the cup format. The patient returns the filled cup to a technician or other person responsible for performing the testing, who then performs the test in accordance with the requirements of the specific device used. The technician records the test results, which are conveyed to the employer. The remaining sample may be thrown away, stored for later use, or sent to a test result confirmation laboratory.

EXAMPLE 5

Well Water Testing for Contamination

This example illustrates how a device and methods of the present invention can be used to test a well as a source of drinking water for contaminants. A sample of drinking water from a well to be tested is obtained and placed into a suitable container. In this format it is desirable to utilize a test device that includes assays for pesticides, ozone, atrazine, arsenic, trihalomethanes, poly-chlorinated biphenyls (PCBs), radon, organophosphates, methyl tertiary butyl ether (MTBE), nitrates, lead, iron, and manganese, as well as biological agents such as *E. coli, Giardia* and *Crytosporidium*. Assays for any chemical or biological agent desired to be tested for can be incorporated into the device.

A sample of water is acquired from the well to be tested. A test strip is then placed into the container holding the water sample. Following the directions for the specific testing device utilized, after a few minutes the color of the test pads is compared to a standard chart. The presence and/or levels of the contaminants being tested for is then determined based on a comparison to the standard chart. If the tests indicate that the well is contaminated with any undesirable agent, an alternate source of water is utilized until the contamination is corrected.

EXAMPLE 6

Food Inspection

This example illustrates how a device and methods of the invention can be utilized in the detection of contaminants in food. A variety of food-born pathogens are of concern to the FDA and local health departments. Meat, dairy products, and other food products are routinely tested at their source of production for contamination with *E. coli* and *Salmonella typhimurium*. In this format it also may be desirable to test for lead, mercury, botulinum toxin, pesticides, chloramphenicol, *Listeria*, as well as other bacterial agents such as *Bacillus cereus, Campylobacter jejuni, Clostridium perfringens, Staphylococcus aureus, Vibrio parahaemolyticus*, and *Yersinia enterocolitica*. The present invention can be used to perform these tests reliably and inexpensively.

In this example a device is utilized that contains a test strip with reagent pads for assaying for *E. coli* and *Salmonella*. An inspector obtains a small sample of beef to be tested, or alternatively swabs the beef, and mixes it with a small amount of buffer in a test tube. The inspector then inserts a test strip into the test tube and waits for 3-5 minutes for the buffer to wick to the second end of the test strip. The inspector then compares the color developed in the reagent pads with a standard chart provided with the package of test strips, and records the test results. The inspector then follows the relevant procedures for testing and reporting of results.

The invention illustratively described herein may be practiced in the absence of any element or elements, limitation or limitations that are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by various embodiments and optional features, modification and variation of the concepts herein disclosed may be resorted to by those skilled in the art, and that such modifications and variations are considered to be within the scope of this invention as defined by the appended claims.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The invention claimed is:

1. A test strip device for analyzing a liquid sample in a lateral flow, comprising:
   a bibulous material for transporting liquid sample through the test strip;
   a hydrophobic member overlaying a first portion of the bibulous material;
   a fiberglass filter member having a first region overlaying a portion of the hydrophobic member and a second region overlaying a second portion of the bibulous material, which is not overlaid by the hydrophobic member, wherein the second region of the filter member is in liquid communication with the second portion of the bibulous material;
   a reagent pad in liquid communication with the first and second regions of the filter member, the reagent pad comprising reagents for producing a detectable signal related to a property of the liquid sample; wherein
   the filter member and the hydrophobic members inhibit backflow of sample from the reagent pad into the bibulous material; and
   a cover.

2. The device of claim 1 wherein the second region of the filter member is positioned between the reagent pad and the second portion of the bibulous material.

3. The device of claim 1 wherein the cover laminates the components of the test strip together.

4. The device of claim 1, wherein the bibulous material comprises a polyamide fibrous absorbent material.

5. The device of claim 1, wherein the reagent pad comprises 3MM filter paper.

6. The device of claim 1, wherein the hydrophobic member comprises an acrylic adhesive.

7. A method of analyzing a liquid sample regarding at least one of its physical and/or chemical properties, comprising:
   exposing to a liquid sample a first end of a device comprising:
      a bibulous material for transporting liquid sample through the test strip;
      a hydrophobic member overlaying a first portion of the bibulous material;
      a fiberglass filter member having a first region overlaying a portion of the hydrophobic member and a second region overlaying a second portion of the bibulous material, which is not overlaid by the hydrophobic member, wherein the second region of the filter member is in liquid communication with the second portion of the bibulous material;

a reagent pad in liquid communication with the first and second regions of the filter member, the reagent pad comprising reagents for producing a detectable signal related to a property of the liquid sample; wherein the filter member and the hydrophobic members inhibit backflow of sample from the reagent pad into the bibulous material; and a cover;

allowing sufficient time for the reagents to react with the sample and provide the detectable signal;

comparing the signal to a standard, determining the at least one of the physical and/or chemical properties of the analyte.

8. The method of claim 7 wherein the second region of the filter member is positioned between the reagent pad and the second portion of the bibulous material.

9. The method of claim 7 wherein the device further comprises a support positioned under the bibulous material.

10. The method of claim 7 wherein the cover laminates the bibulous material, filter element, and reagent pad together.

11. The method of claim 7 wherein the sample is selected from the group consisting of: a biological sample, an environmental sample, and a food or beverage sample.

12. The method of claim 11 wherein the sample is a biological sample selected from the group consisting of: blood, serum, plasma, saliva, oral fluid, sweat, urine, feces, spinal fluid, vaginal swabs, mucus, tissue, milk, wine, food, water and soil.

13. The method of claim 11 wherein the sample is a liquid or a liquid derived from a solid.

14. The method of claim 7 wherein the analyte is selected from the group consisting of: an oxidizing agent, a reducing agent, a nitrate, a nitrite, glutaraldehyde, pyridinium chlorochromate, heavy metals, toxic metals, toxic chemicals, blood, a blood component, a blood product, glucose, ketones, peroxide, protein, creatinine, urobilinogen, bilirubin, bacteria, bacterial components and bacterial products.

15. The method of claim 7 wherein the physical property is pH or specific gravity.

16. The method of claim 7, wherein the bibulous material comprises a polyamide fibrous absorbent material.

17. The method of claim 7, the hydrophobic member comprises an acrylic adhesive.

* * * * *